United States Patent [19]

Gorman et al.

[11] 4,173,702
[45] Nov. 6, 1979

[54] 7-(5-AMINO-5-CARBOXYVALER-AMIDO)-3-(CARBAMOYLOXYMETHYL)-7-METHOXY-3-CEPHEM-4-CARBOXYLIC ACID

[75] Inventors: Marvin Gorman; Calvin E. Higgens; Ramakrishnan Nagarajan, all of Indianapolis, Ind.

[73] Assignee: Eli Lilly and Company, Indianapolis, Ind.

[21] Appl. No.: 62,390

[22] Filed: Aug. 10, 1970

Related U.S. Application Data

[63] Continuation-in-part of Ser. No. 849,395, Aug. 12, 1969, abandoned.

[51] Int. Cl.$^2$ .............................................. C07D 501/20
[52] U.S. Cl. ...................................... 544/21; 544/16; 424/246
[58] Field of Search .......................................... 544/21

Primary Examiner—Nicholas S. Rizzo
Attorney, Agent, or Firm—Kathleen R. S. Page; Everet F. Smith

[57] ABSTRACT

Antibiotic A16886I and antibiotic A16886II and their salts, having antibacterial and anthelmintic activity, prepared by fermentation of Streptomyces clavuligerus NRRL 3585.

3 Claims, 2 Drawing Figures

FIG. I

7-(5-AMINO-5-CARBOXYVALER-AMIDO)-3-(CARBAMOYLOXYMETHYL)-7-METHOXY-3-CEPHEM-4-CARBOXYLIC ACID

CROSS-REFERENCE TO RELATED APPLICATION

This is a continuation-in-part of our copending application Ser. No. 849,395, filed Aug. 12, 1969, now abandoned.

SUMMARY OF THE INVENTION

Fermentation of *Streptomyces clavuligerus* produces new antibiotic substances designated herein as antibiotic A16886. The salts of antibiotic A16886 are readily obtained by reaction of antibiotic A16886 with a suitable acid or base. Antibiotic A16886 and its salts exhibit antibacterial and anthelmintic activity. The antibacterial activity is exhibited primarily against gram-negative organisms, but some activity is also exhibited against gram-positive organisms. Antibiotic A16886 is also effective in controlling disease caused by plant-pathogenic bacteria.

DESCRIPTION OF PREFERRED EMBODIMENTS

Figure 1:
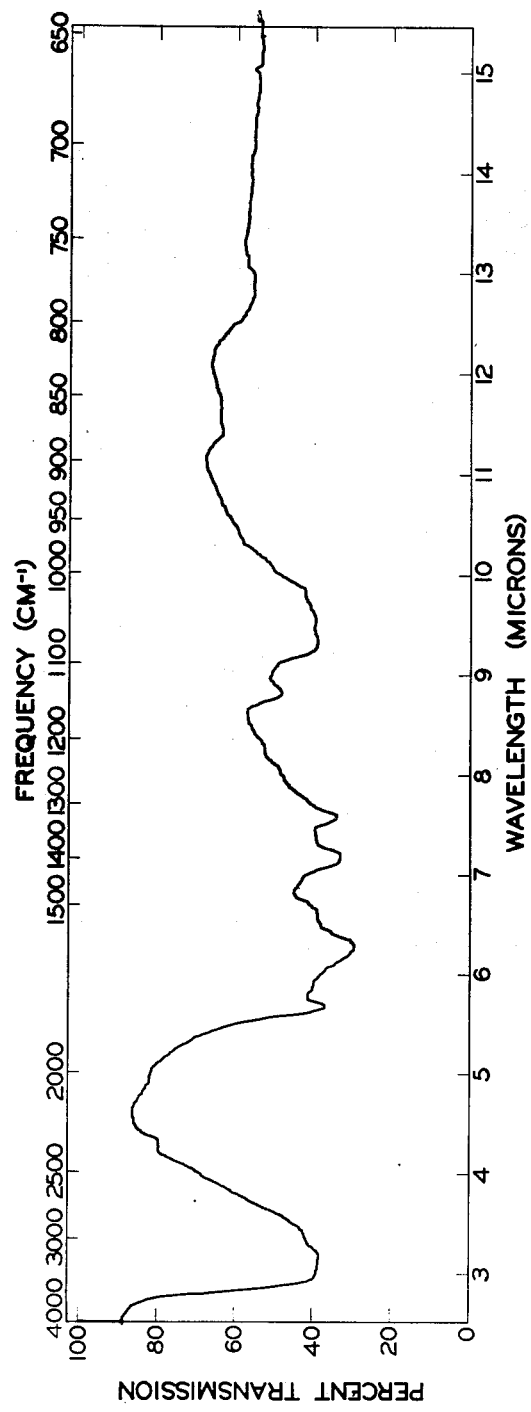

Antibiotic A16886, a sulfur-containing peptide antibiotic, is an amphoteric molecule produced by cultivating under controlled conditions *Streptomyces clavuligerus* NRRL 3585.

As in the case with many antibiotic-producing cultures, fermentation of *Streptomyces clavuligerus* NRRL 3585 results in the production of a number of antibiotic substances called "factors." Antibiotic A16886, as presently obtained from the fermentor, comprises two major antibiotic substances referred to herein as A16886I and A16886II or as factor I and factor II. Other antibiotic substances have been observed in some fermentations, but these have been present in only small amounts. Hence, the unmodified term "antibiotic A16886" is employed herein to refer to the antibiotic as obtained from the fermentor and ordinarily comprising from 1 to 99 percent of factor I and from 99 to 1 percent of factor II in addition to other minor factors, the total percentage being 100. Accordingly, in the discussions herein of utility and modes of usage, the term "antibiotic A16886" applies equally to individual factors as well as to mixtures inasmuch as the properties of the individual factors and mixtures thereof are similar.

Antibiotic A16886 can be utilized as such or as a salt, for example, an acid addition salt or a salt with a cation. In the instance of a salt with a cation, the salt can be either a mono or di salt. It is often preferred to prepare salts directly in the purification process so that the antibiotic as separated is in salt form. Antibiotic A16886 has been separated in this manner, as the monoammonium salt, and for that reason, is hereinbelow characterized as the monoammonium salt.

Certain characterizations have been made on the mixture of factors I and II. For example, a number of qualitative chemical tests have been carried out with a mixture of the monoammonium salt of factor I and the monoammonium salt of factor II: positive tests were exhibited with ninhydrin, Pan-Dutscher, Benedict, Molisch, Fehling, dansyl chloride, iodine, and ferric chloride reagents, but negative tests were observed with biuret and Sakaguchi reagents. A mixture of the monoammonium salts of factors I and II dried at room temperature in vacuo over anhydrous calcium chloride for about 15 hours, exhibited an optical rotation $[\alpha]_D^{25} + 110.1°$ (C=1 percent w./v. in water). A mixture of the monoammonium salts of factors I and II of antibiotic A16886 is stable at pH 3–8 at 6° C. for 8 days and relatively stable at pH 3–8 at 25° C. for 2 days. Biological activity is slowly lost at pH 3–8 at a temperature of 25° C., half being lost at 4 days.

In addition, the monoammonium salts of factors I and II have been separately characterized. The monoammonium salt of antibiotic A16886I is an off-white, fluffy, amorphous solid, softening between 190° and 300° C., with a color change to dark brown; it is very soluble in water, slightly soluble in lower alkanols, and essentially insoluble in acetonitrile and other organic solvents. The specific optical rotation $[\alpha]_D^{25}$ of the monoammonium salt of antibiotic A16886I, dried at room temperature in vacuo over anhydrous calcium chloride for about 15 hours, was found to be +153.6° (C=1 percent, w./v. in water). Electrometric titration of the monoammonium salt of antibiotic A16886I in a 66 percent dimethylformamide-water solution at an initial pH of 6.50 revealed the presence of four titratable groups: $pK'a_1 = 4.1$; $pK'a_2 = 5.2$; $pK'a_3 = 9.3$; and $pK'a_4 = 10.5$. The apparent molecular weight, calculated from the titration data, is about 530.

Elemental analysis of the monoammonium salt of A16886I, dried in vacuo at about 80° C. over phosphorus pentoxide, gave the following values:

| Element | Percent |
| --- | --- |
| Carbon | 40.26 |
| Hydrogen | 5.91 |
| Nitrogen | 13.98 |
| Oxygen | 33.37 |
| Sulfur | 7.21 |

Analysis of the monoammonium salt of antibiotic A16886I shows a methoxyl content of 5.02 percent; the presence of the methoxyl group was confirmed by a singlet at 3.53 ppm. in the NMR spectrum. A Van Slyke test for amino nitrogen of the monoammonium salt of antibiotic A16886I showed 5.3 percent.

The NMR spectrum of A16886I in $D_2O$ showed the following characteristics: 5.19 ppm. (1H, singlet); 4.94, 4.74 ppm. (2H, AB quartet, J=13 Hz); 4.0–4.2 ppm. (1H, multiplet); 3.68, 3.32 ppm. (2H, AB quartet, J=18 Hz); 3.53 ppm. (3H, singlet); 2.6–2.4 ppm. (2H, multiplet); 2.1–1.6 ppm. (4H, multiplet).

The infrared absorption spectrum of the monoammonium salt of antibiotic A16886I in a mineral oil mull is shown in FIG. 1 of the accompanying drawings. The distinguishable bands in the infrared spectrum over the range of 2.0 to 15.0 microns are as follows: 3.10, 5.68, 6.30, 6.60, 7.20, 7.60, 8.83, 9.35, 9.60, 9.85, 11.60, and 12.90 microns.

The ultraviolet absorption spectrum of the monoammonium salt of antibiotic A16886I in aqueous solution shows absorption maxima at 242 m$\mu$ ($E_{1\ cm}^{1\%} = 132$) and at 264 m$\mu$ ($E_{1\ cm}^{1\%} = 165$); circular dichroism was also measured in aqueous solution and showed a positive Cotton effect at 263 m$\mu$ and a negative Cotton effect at 236 m$\mu$.

Paper chromatography of the ammonium salt of antibiotic A16886I on Whatman No. 1 paper gave an $R_f$ value of 0.41 in a solvent system of propanol, acetonitrile, and water in a volume ratio of 1:1:1. Bioautographs were obtained by placing the paper chromatograph on agar plates seeded with *Salmonella gallinarum* as the test organism.

When the monoammonium salt of A16886I is subjected to thin-layer chromatography on silica gel plates in 70 percent aqueous acetonitrile, utilizing a ninhydrin spray as a detector, it has an $R_f$ value of about 0.51; on cellulose plates in acetonitrile:isopropanol:water (1:1:1), utilizing the same procedure for detection, it has an $R_f$ value of 0.36.

Amino acid analysis of an acid hydrolysate of antibiotic A16886I, run by the Spackman-Moore-Stein technique, showed two ninhydrin reacting peaks, one of which was eluted identically with glycine (0.61 μmoles/mg.), the other of which was eluted just prior to glycine and was identified as α-aminoadipic acid (1.97 μmoles/mg.).

Based on the various foregoing physical characteristics, the structure of antibiotic A16886I has been determined to be as follows:

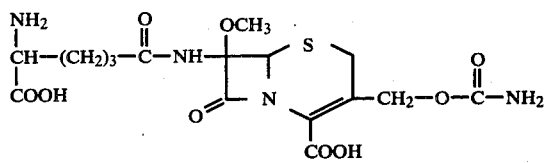

which structure is designated 7-(5-amino-5-carboxyvaleramido)-3-(carbamoyloxymethyl)-7-methoxy-3-cephem-4-carboxylic acid.

The monoammonium salt of antibiotic A16886II has also been separately characterized. It is an off-white, fluffy, amorphous solid, softening between 190° and 300° C., with a color change to dark brown; it is very soluble in water, slightly soluble in lower alkanols, and essentially insoluble in acetonitrile and other organic solvents. The specific optical rotation $[\alpha]_D^{25}$ of the monoammonium salt of antibiotic A16886II, dried at room temperature in vacuo over anhydrous calcium chloride for about 15 hours, was found to be +86.2° (C=1 percent, w./v. in water).

Electrometric titration of the monoammonium salt of antibiotic A16886II in a 66 percent dimethyl formamide-water solution at an initial pH of 7.7, revealed the presence of four titratable groups: pK'$_{a1}$=4.4; pK'$_{a2}$=5.7; pK'$_{a3}$=9.6; pK'$_{a4}$=10.4. In like titration of a later sample, except that it showed an initial pH of 6.8, the respective values were pK'$_{a1}$=4.0; pK'$_{a2}$=5.3; pK'$_{a3}$=9.2; and pK'$_{a4}$=10.5. The apparent molecular weight of the monoammonium salt of antibiotic A16886II, calculated from the titration data, is about 528.

Elemental analysis of the monoammonium salt of antibiotic A16886II, dried in vacuo at about 80° C. over phosphorus pentoxide, gave the following values:

| Element | Percent |
| --- | --- |
| Carbon | 41.01 |
| Hydrogen | 5.64 |
| Nitrogen | 15.75 |
| Oxygen | 29.28 |
| Sulfur | 7.04 |

Analysis of the monoammonium salt of A16886II showed no methoxyl content, and, unlike factor I, no signal attributable to the methoxyl group was seen in the NMR spectrum on the monoammonium salt of A16886II. A Van Slyke test for amino nitrogen on the monoammonium salt of antibiotic A16886II showed 5.1 percent.

The NMR spectrum of A16886II in D$_2$O showed the following characteristics: 5.67 ppm. (1H, doublet, J=5 Hz); 5.15 ppm. (1H, doublet, J=5 Hz); 4.90, 4.68 ppm. (2H, AB quartet, J=13 Hz); 3.9–3.7 (1H, multiplet); 3.69, 3.39 (2H, AB quartet, J=18 Hz); 2.6–2.3 (2H, multiplet); 2.1–1.5 (4H, multiplet).

Figure 2:
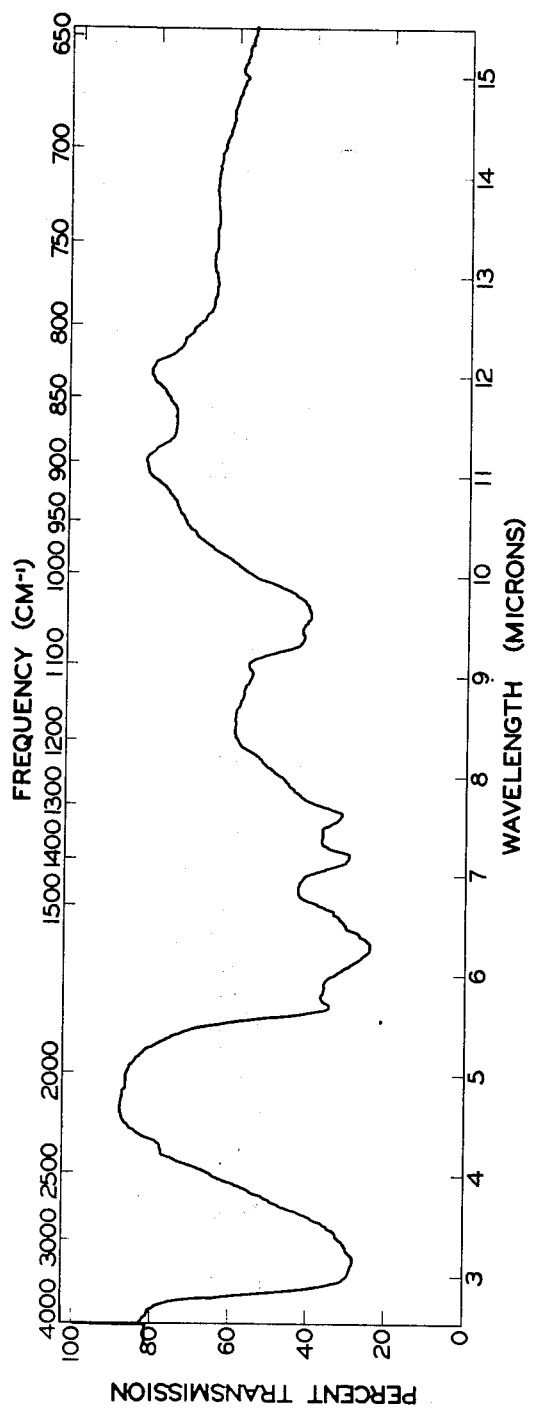

The infrared absorption of the monoammonium salt of antibiotic A16886II in a mineral oil mull is shown in FIG. 2 of the accompanying drawings. The distinguishable bands in the infrared spectrum over the range of 2.0 to 15.0 microns are as follows; 3.15, 5.70, 6.30, 7.22, 7.64, 9.05, 9.40, 9.65, and 11.60 microns.

The ultraviolet absorption spectrum of the monoammonium salt of antibiotic A16886II in aqueous solution shows an absorption maximum of 260 mμ (E$_1$ cm$^{1\%}$=148); circular dichroism was also measured in aqueous solution and showed a positive Cotton effect at 258 mμ and a negative Cotton effect at 228 mμ.

Paper chromatography of the monoammonium salt of antibiotic A16886II on Whatman No. 1 paper gave an $R_f$ value of 0.33 in a solvent system of propanol, acetonitrile, and water in a volume ratio of 1:1:1. Bioautographs were obtained by placing the paper chromotograph on agar plates seeded with *Salmonella gallinarum* as the test organism.

When the monoammonium salt of A16886II is subjected to thin-layer chromatography on silica gel plates in 70 percent aqueous acetonitrile, utilizing a ninhydrin spray or bioautographic method as a detector, it has an $R_f$ value of about 0.42; on cellulose plates in acetonitrile:isopropanol:water (1:1:1), utilizing the same procedure for detection, it has an $R_f$ value of 0.29.

Amino acid analysis of an acid hydrolysate of antibiotic A16886II, run by the Spackman-Moore-Stein technique, showed primarily only one ninhydrin reacting peak; it was eluted just prior to glycine, and as in the instance of antibiotic A16886I, was identified as α-aminoadipic acid (2.1 μmoles/mg.). However, there was also a very minor peak which was eluted identically with glycine. A later sample was analyzed in like manner and showed values of 2.1 μmoles/mg. and 0.13 μmoles/mg., respectively.

Based on the various foregoing physical characteristics, the structure of antibiotic A16886II has been determined to be as follows:

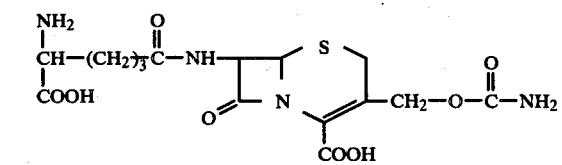

which structure is designated 7-(5-amino-5-carboxyvaleramido)-3-(carbamoyloxymethyl)-3-cephem-4-carboxylic acid.

In addition to the foregoing, each of factors I and II of the monoammonium salt of antibiotic A16886 was subjected to paper chromatography and thin-layer chromatography in a number of other solvent systems with the following results:

| Solvent System | $R_f$ value | |
|---|---|---|
| | Factor I | Factor II |
| Paper Chromatography | | |
| Ethanol:water (80:20) with 1.5% sodium chloride, paper impregnated with 1N sodium sulfate | .38 | .33 |
| Butanol saturated with water | immobile | immobile |
| Butanol saturated with water plus 2% p-toluenesulfonic acid | .39 | .32 |
| Methyl isobutyl ketone saturated with water | immobile | immobile |
| Methyl isobutyl ketone saturated with water plus 2% p-toluene-sulfonic acid | immobile | immobile |
| Methyl isobutyl ketone saturated with water plus 2% piperidine | immobile | immobile |
| Acetonitrile | immobile | immobile |
| Propanol:acetonitrile:methanol:water (4:3:2:1) | immobile | immobile |
| Propanol:pyridine:acetic acid:water (15:10:3:12) | .32 | .27 |
| Propanol:pyridine:acetic acid:acetonitrile:water (45:30:9:40:36) | .21 | .15 |
| Butanol:acetic acid:water (3:1:1) | .20 | .17 |
| Ethyl acetate:acetic acid:water (3:1:1) | .29 | .22 |
| Propanol:water (70:30) | .17 | .17 |
| Acetonitrile:water (70:30) | .72 | .65 |
| Water:ethanol:acetic acid (70:42:6) | .82 | .82 |
| Thin-Layer Chromatography | | |
| Acetonitrile-water (7:3) on cellulose plates | .35 | .29 |

Antibiotic A16886 and its salts have an inhibitory action against the growth of both gram-positive and gram-negative bacteria. The levels at which antibiotic A16886 as a partially purified mixture of the monoammonium salts of factors I and II shows inhibition against the growth of illustrative organisms are set forth in Table I. The inhibitory levels were determined by the agardilution test or by the broth-dilution test (identified in the table by the letters "a.d." and "b.d.", respectively).

In the agar dilution test, the test organism was streaked on a series of agar plates containing various concentrations of the monoammonium salts of factors I and II of antibiotic A16886 to determine the minimum concentrations in mcg./ml. (micrograms per milliliter) in the agar substrate which inhibited the growth of the organism over a period of forty-eight hours (seventy-two hours in the case of the plant-pathogen organisms).

In the broth dilution test, a series of tubes containing varied concentrations of the monoammonium salts of factors I and II of antibiotic A16886 was inoculated with the test organism to determine the minimum concentration in mcg./ml. in the broth substrate which inhibited organism growth for a period of about twenty hours.

TABLE I

| Test Organism | Inhibitory Concentration mcg./ml. |
|---|---|
| Escherichia coli O127 | 0.39 b.d. |
| Proteus PR-6 | 0.78 a.d. |
| Salmonella typhimurium S-4 | 0.78 a.d. |
| Klebsiella sp. K-1 | 1.56 a.d. |
| Pseudomonas sp. X239 | >100 a.d. |
| Salmonella typhosa T-63 | 0.78 b.d. |
| Staphylococcus aureus 3055 | 25.00 a.d. |
| Streptococcus pyogenes C203 | 6.25 a.d. |
| Bacillus subtilis X12.1 | 1.56 a.d. |
| Staphylococcus aureus 3150 | 50.00 a.d. |

No binding by horse serum was noted in any of the above tests. As can be seen from the above table, antibiotic A16886 as a mixture of the monoammonium salts of factors I and II exhibits activity against gram-positive and gram-negative bacterial organisms.

Antibiotic A16886 was further evaluated for antibacterial activity in a test employing the Bauer-Kirby disc diffusion method. The evaluation was made on the monoammonium salts of separated factors I and II. The results, expressed in terms of millimeters of the zone of inhibition at a specified antibiotic concentration, were as set forth below in Table II.

TABLE II

| Organism | Factor I μg./disc | | | | | | Factor II μg./disc | | | | | |
|---|---|---|---|---|---|---|---|---|---|---|---|---|
| | 30 | 10 | 5 | 2.5 | 1.0 | 0.5 | 30 | 10 | 5 | 2.5 | 1.0 | 0.5 |
| Escherichia coli 0127 | 25.6 | 20.7 | 18.6 | 15.9 | 12.7 | 8.4 | 19.7 | 15.9 | 12.9 | 9.4 | 0 | 0 |
| Escherichia coli EC 25 | 19.6 | 15.1 | 12.5 | 9.1 | 0 | 0 | 11.9 | 7.7 | 0 | 0 | 0 | 0 |
| Proteus sp. PR6 | 23.2 | 19.0 | 16.7 | 13.6 | 9.9 | 0 | 22.2 | 16.7 | 13.6 | 10.4 | 0 | 0 |
| Proteus sp. PR7 | 14.0 | 10.4 | 0 | 0 | 0 | 0 | 7.1 | 0 | 0 | 0 | 0 | 0 |
| Salmonella typhosa SA 12 | 27.2 | 22.8 | 19.9 | 16.9 | 11.3 | 8.0 | 23.8 | 18.7 | 15.6 | 12.3 | 7.5 | 0 |
| Salmonella typhosa SA 16 | 24.2 | 19.6 | 16.2 | 13.1 | 9.3 | 0 | 19.3 | 13.4 | 11.0 | 7.5 | 0 | 0 |
| Klebsiella-Aerobacter KA 14 | 23.0 | 18.8 | 15.4 | 11.4 | 7.6 | 0 | 20.1 | 13.7 | 10.8 | 0 | 0 | 0 |
| Klebsiella-Aerobacter KA 25 | 22.1 | 15.8 | 12.3 | 9.0 | 0 | 0 | 15.6 | 10.1 | 7.4 | 0 | 0 | 0 |
| Pseudomonas sp. Ps 24 | 23.0 | 18.2 | 15.7 | 13.2 | 10.1 | 0 | 20.2 | 15.4 | 12.3* | 9.3* | 0 | 0 |
| Pseudomonas sp. Ps 30 | 0 | 0 | 0 | 0 | 0 | 0 | 0 | 0 | 0 | 0 | 0 | 0 |
| Staphylococcus aureus 3055 | 0 | 0 | 0 | 0 | 0 | 0 | 12.4 | 0 | 0 | 0 | 0 | 0 |
| Staphylococcus aureus 3074 | 0 | 0 | 0 | 0 | 0 | 0 | 10.1 | 0 | 0 | 0 | 0 | 0 |

*Satellite colonies within zone of inhibition

Antibiotic A16886 and its salts also exhibit in vivo activity against a number of the above organisms and hence are useful in controlling infections caused by such organisms in host animals. Mammalian toxicity is low; the $LD_{50}$ is >5 grams/kilogram, and daily subcutaneous administration of 350 milligrams/kilogram to a group of 10 rats for a period of fourteen days resulted in no deaths and negligible signs of toxicity. Antibiotic A16886 as a mixture of the monoammonium salts of factors I and II exhibited the following $ED_{50}$ values in mice infected with the respective organism:

TABLE III

| Organism | $ED_{50}$ | |
|---|---|---|
| Escherichia coli 0127 | 13.8 | (Administration was by the sub-cutaneous route) |
| Salmonella typhosa T-63 | 15.6 | |
| Klebsiella K-1 | 10.2 | |
| Proteus PR-6 | 7.3 | |

In addition, antibiotic A16886 and its salts exhibit activity against plant-pathogenic bacteria. Thus, for example, antibiotic A16886 and its salts control such plant-pathogenic bacterial infections as bacterial wilt, bacterial spot, and bacterial blight.

The precise manner of application of antibiotic A16886 or a salt thereof to plants is not critical. Generally, initial contact of the causative organism is with plant foliage; for this reason, foliar application of antibiotic A16886 or a salt thereof is often preferred. However, antibiotic A16886 and salts thereof are translocated; consequently, application can also be made to stems, flowers, seeds, roots, or other plant parts to obtain bactericidal effect throughout plants.

The present method for controlling plant-pathogenic bacteria comprises applying to a plant exposed to the bacteria an effective amount of antibiotic A16886 or a salt thereof. It is not critical to this method that the antibiotic be employed as a single factor; each of factor I and factor II can be used alone and gives good results. Alternately, a mixture of factors can be employed. Antibiotic A16886 or a salt thereof can be employed without modification, but generally it is preferred for plant-treating purposes to employ a formulation comprising the antibiotic A16886 or a salt thereof and one or more adjuvants. In preparing such formulations, antibiotic A16886 or its salt can be modified with water or other liquid carriers, organic solvents, surface-active agents including solid surface-active agents, or inert, finely divided solids or inert, granular solids. The exact concentration of antibiotic A16886 or a salt thereof in such a formulation is not critical and will vary with the particular purpose for which the formulation is designed. Generally, for foliar application for control of typical plant-pathogenic bacterial infections, conconcentrations of antibiotic A16886 or a salt thereof from 10 ppm. to 1000 or more ppm. give good results. In the case of dusts for foliar application, preferred concentrations of antibiotic are 0.1–10.0 percent.

In preparing liquid formulations, antibiotic A16886 or a salt thereof can be compounded with a suitable liquid and a surface-active dispersing agent to produce emulsifiable concentrates which can be further diluted with water or other liquid to form spray mixtures. Preferred dispersing agents which can be employed in these compositions include the non-ionic emulsifiers such as the condensation products of alkylene oxides with the inorganic acids, polyoxyethylene derivatives of sorbitan esters, complex ether alcohols, and the like. Suitable organic liquids which can be employed in the composition include petroleum oils and distillates, toluene, and synthetic organic oils. The surface-active dispersing agents are usually employed in liquid compositions in the amount of from 0.1 to 20 percent by weight of the combined weight of the dispersing agent and active compound. In the preparation of dust compositions, antibiotic A16886 or a salt thereof can be compounded with any of the finely divided solids or granules typically used in agricultural chemical formulations.

When operating in accordance with the present invention, antibiotic A16886 or a salt thereof or a composition containing antibiotic A16886 or a salt thereof can be applied to the organisms to be controlled, or to their habitats in any convenient fashion, e.g., by means of hand dusters or sprayers. Applications to the aboveground portions of plants conveniently can be carried out with powder dusters, boom sprayers, high-pressure sprayers, and spray dusters. In foliar applications, the employed compositions should not contain any appreciable amount of phytotoxic diluents. In large-scale operations, dusts or low-volume sprays can be applied from airplanes.

The following examples illustrate this embodiment of the present invention and will enable those skilled in the art to practice the same.

EXAMPLE 1

ERWINIA AMYLOVORA AND PSEUDOMONAS SOLANACEARUM, IN VITRO

Antibiotic A16886 (as a mixture of the monoammonium salt of factor I and the monoammonium salt of factor II) was evaluated in vitro for inhibition of *Erwinia amylovora* and *Pseudomonas solanacearum*. Each of the organisms was separately incorporated in standard nutrient agar, and the resulting agars poured into a plurality of plates and permitted to solidify. Treatment was then made, different plates being treated by different methods. In one method of treatment, 0.1 milliliter of test solution was pipetted into each of two small steel cylinders setting upright on a given agar surface. In the other method, 0.1 milliliter of test solution was impregnated onto each of two filter assay discs which were placed onto a given agar surface. The test solution for both methods of treatment was prepared by dissolving the appropriate quantity of antibiotic A16886 in glass-distilled water. The results, expressed as the diameter of the zone of inhibition, were as set forth in the following table:

TABLE IV

| | DIAMETER - ZONE INHIBITION MEASUREMENT IN MILLILITERS | | | |
|---|---|---|---|---|
| | Steel Cylinders[A] | | Filter Discs[B] | |
| Treatment | E. amylovora | P. solanacearum | E. amylovora | P. solanacearum |
| A16886 - 10 ppm. | 6—6 | 16—17 | 13—13 | 20—21 |
| A16886 - 50 ppm. | 12-14 | 25—25 | 16—17 | 30—30 |
| A16886 - 100 ppm. | 15-16 | 30—30 | 20—20 | 34-35 |
| Control (distilled water) | 6—6 | 6—6 | 13—13 | 13—13 |

[A]includes the size of cylinder - 6mm.; therefore, a zone size of 6 mm. indicates no growth inhibition.
[B]includes the size of filter disc - 13 mm.; therefore, a zone size of 13 mm. indicates no growth inhibitic

EXAMPLE 2

PSEUDOMONAS SOLANACEARUM, FOLIAR SPRAY

Antibiotic A16886 (as a mixture of the monoammonium salt of factor I and the monoammonium salt of factor II) was also evaluated in vivo for the control of *Pseudomonas solanacearum* on tomato plants. In this evaluation, antibiotic A16886 monoammonium salt was formulated in a plurality of aqueous formulations uniformly containing 1 percent of ethanol and 0.1 percent of a surface-active agent (a polyoxyethylene derivative of fatty acid partial ester of sorbitol anhydride) but containing various concentrations of antibiotic A16886. Thirty-day-old tomato plants were used in the evaluation, 2 plants/pot/treatment. Plants in each pot were treated with one of the treating solutions, were allowed to air dry, and were then inoculated with a medium sustaining an active growth of *Pseudomonas solanacearum*. All plants were held for 24 hours in a moist chamber, then removed and held for 7 days under good agricultural conditions. At the end of this seven-day period, all of the plants were observed to determine presence, and if present, degree, of infection. The results were as reported in the following table; disease was rated on a scale of 0 to 4, 0 indicating no control, 4 representing complete control, with each plant rated separately.

TABLE V

|  | *Pseudomonas solanacearum* Disease Rating | |
| --- | --- | --- |
| Control (1% EtOH + 0.1% surface-active agent) | 0 | 0 |
| A16886 - 400 ppm. | 2+ | 3+ |
| A16886 - 200 ppm. | 2+ | 2+ |

The control plants exhibited an extensive *Pseudomonas solanacearum* infection.

EXAMPLE 3

PSEUDOMONAS GLYCINIA, BARE-ROOT SOAK

Antibiotic A16886 (as a mixture of the monoammonium salt of factor I and the monoammonium salt of factor II) was evaluated for the control of *Pseudomonas glycinia* by means of bare-root soaking solutions containing the A16886. There were two soaking solutions, one containing 200 parts per million of antibiotic A16886, the other containing 400 parts per million of antibiotic A16886. Ten-day-old soybean plants were inoculated with *Pseudomonas glycinia*, and the roots of all plants maintained throughout the evaluation in aqueous solutions. Initially, the inoculated plants were placed in 50 milliliters of solution, one group of plants in the 200 ppm. solution, a second group of plants in the 400 ppm. solution, a third group of plants in water to serve as a control. The roots were soaked for 24 hours, with aeration during this period. The plants, with roots still in the several solutions, were then incubated for twenty-four hours. Thereafter, the plants were removed from the incubation chamber and held for a period of a week. Beginning approximately with the incubation period and continuing throughout the week, a solution containing nutrients was added to the roots as needed to maintain the plants in a viable condition. At the end of the week period, the plants were observed to determine the extent of development of *Pseudomonas glycinia*; disease was rated on a scale of 0 to 4, 0 indicating no control, 4 representing complete control. The results were as set forth in the following table:

TABLE VI

|  | Disease Rating of *Pseudomonas glycinia* |
| --- | --- |
| Control | 0 |
| A16886 - 200 ppm. | 3+ |
| A16886 - 400 ppm. | 2+ |

EXAMPLE 4

XANTHOMONAS PHASEOLI VAR. SOJENSIS, FOLIAR SPRAY

In a first evaluation, ten-day-old soybean plants were inoculated by lightly water-soaking the lower leaf surfaces of the primary leaves with a suspension of *Xanthomonas phaseoli* var. *sojensis*. Two hours later, the foliage was sprayed with a spray solution, one group of inoculated plants being treated with a solution containing 100 parts per million of antibiotic A16886, a second group, with a solution containing 500 parts per million of antibiotic A16886. Antibiotic A16886 was formulated in water with 353 parts per million of a blend of sulfonate-nonionic liquid emulsifiers.

In a second evaluation, the foliage of ten-day-old soybean plants was sprayed with a spray solution containing either 100 or 500 parts of antibiotic A16886, and, two hours later, inoculated by the same procedures used in the first evaluation. Formulation of antibiotic A16886 was the same as in the first evaluation. All samples of antibiotic A16886 were a mixture of the monoammonium salt of factor I and the monoammonium salt of factor II.

The plants were maintained under good agricultural conditions for a period of about 11 days and then observed for the presence or absence of *Xanthomonas phaseoli* var. *sojensis*. The results were as set forth in the following table, with rating being on a 0 to 4 scale as in the preceding examples.

TABLE VII

|  | Disease Rating Average Per Treated Group of Plants *Xanthamonas phaseoli* var. *sojensis* | |
| --- | --- | --- |
|  | Inoculate then spray | spray then inoculate |
| Control (water alone) | 0 | 0 |
| Control (water plus blend of emulsifier) | 0 | 0 |
| A16886 - 100 ppm. | 2 | 4 |
| A16886 - 500 ppm. | 3+ | 4 |

EXAMPLE 5

PSEUDOMONAS PHASEOLICOLA, FOLIAR SPRAY

All surfaces of twenty-day-old red kidney bean plants were sprayed with an aqueous formulation containing 400 parts per million of antibiotic A16886 (as a mixture of the monoammonium salt of factor I and the monoammonium salt of factor II), and 0.1 percent of a surface-active agent (a polyoxyethylene derivative of a fatty acid partial ester of sorbitol anhydride). The sprayed plants were permitted to dry and then inoculated with *Pseudomonas phaseolicola* inoculation was achieved by water-soaking of the lower leaf surface of one leaflet of each of the first and second trifoliate leaves with an aqueous bacterial suspension at 30 percent light transmission on a Bausch and Lomb Spectronic 20. The plants were subsequently held in a moist chamber for twenty-four hours, then removed and held under good agricultural conditions for 14 days. At the end of this period, all plants were observed; in the treated group of plants, there was a moderate control of *Pseudomonas phaseolicola*, whereas in the control group, there was an extensive development of the disease.

EXAMPLE 6

PSEUDOMONAS SOLANACEARUM, SEPARATE FOLIAR OR STEM SPRAY

Antibiotic A16886 (as a mixture of the monoammonium salt of factor I and the monoammonium salt of factor II) was formulated in water with a blend of two sulfonate-nonionic liquid emulsifiers to obtain two treating solutions, one containing 100 parts per million of A16886, the other containing 400 parts per million of antibiotic A16886, and each containing 353 parts per million of the emulsifier blend. Groups of twenty-eight-day-old tomato plants were employed; in one set of evaluations, the solution was applied to the stems only, and in the second set of evaluations, the solution was applied to the leaves only. Two hours after treatment by either method, the plants were inoculated by inserting a toothpick soaked in a broth culture of *Pseudomonas solanacearum* into the stem at the cotyledons. The plants were held under good agricultural conditions for 10 days and then observed to determine control of the disease. The results, on a scale of 0–4, with 0 indicating no control and 4 indicating complete control, were as follows:

TABLE VIII

|  | *Pseudomonas solanacearum* Disease Rating | | | |
|---|---|---|---|---|
|  | Leaves, only | treated | Stems, only | treated |
| Control (water plus 353 ppm. of blend of emulsifiers) | 0 | 1 | 0 | 1 |
| A16886 - 100 ppm. | 3 | 4 | 3 | 4 |
| A16886 - 400 ppm. | 4 | 4 | 4 | 4 |

EXAMPLE 7

PSEUDOMONAS SOLANACEARUM, FOLIAR SPRAY

Further evaluations were conducted in accordance with the procedure reported in Example 2, except that antibiotic A16886I and A16886II were evaluated separately (but each as the monoammonium salt). The results were as set forth in the following table.

TABLE IX

|  | *pseudomonas solanacearum* Disease Rating |
|---|---|
| Control | 0 |
| A16886I - 100 ppm. | 4 |
| A16886I - 10 ppm. | 2 |
| A16886II - 100 ppm. | 4 |
| A16886II - 10 ppm. | 1 |

The control plants exhibited a light infection of *Pseudomonas solanacearum*.

EXAMPLE 8

PSEUDOMONAS SOLANACEARUM, FOLIAR SPRAY

A16886I monoammonium salt was evaluated again in the procedure of Example 2 at concentrations in the treating solution of 100, 200, and 400 ppm. of A16886I. A rating of 4 was obtained at each of the concentrations. There was a heavy infestation of *Pseudomonas solanacearum* on the control plants.

EXAMPLE 9

XANTHOMONAS VESICATORIA, FIELD TRIAL

A mixture of the monoammonium salt of A16886I and the monoammonium salt of A16886II was tested under field conditions for the control of *Xanthomonas vesicatoria* (bacterial spot) on mature bearing tomato plants. The mixture of the two salts was dispersed in water at a concentration of 100, 200, or 400 parts per million and applied to the plants at the rate of 75 gallons per acre. Application was made with a $CO_2$ sprayer at 50 psi. Plants were sprayed twice, on successive days; after the second spray had dried, all plants were wounded by sand blasting and then within one minute the plants were inoculated with a bacterial inoculum of *Xanthomonas vesicatoria.* Three days later, a third spray application of the aqueous formulation of A16886 was made. Readings were made one week and two weeks after the last spray treatment. Controls consisted of groups of plants (1) sand blasted and inoculated; (2) sand blasted only; (3) untreated; and (4) treated with streptomycin (on the same three-day spraying schedule, at a concentration of 100, 200, or 400 parts per million of aqueous solution, using a rate of 75 gallons per acre), sand blasted, and inoculated. The results were as set forth in the following table, in which crop injury is reported on a scale of 0–10, with 0=no injury and 10=dead plants; and control of bacterial spot is reported on a percentage basis.

TABLE X

| | Concentrations in Parts/Million of Treating Solution | Crop Injury Ratings First Reading | Second Reading | Percent Bacterial Spot Control First Reading | Second Reading |
|---|---|---|---|---|---|
| A16886 | 100 | 0 | 0 | 88 | 46 |
| A16886 | 200 | 0 | 0 | 85 | 63 |
| A16886 | 400 | 0 | 0 | 97 | 80 |
| Streptomycin | 100 | 0 | 0 | 83 | 57 |
| Streptomycin | 200 | 0 | 0 | 81 | 37 |
| Streptomycin | 400 | 0 | 0 | 83 | 59 |
| Control (Sand blasted and inoculated) | 0 | 0 | 0 | 0 (14)* | 0 (47)* |
| Control (Sand blasted only) | 0 | 0 | 0 | 0(0.3)* | 0 (8)* |
| Control (Untreated) | 0 | 0 | 0 | 0 (0)* | 0 (6)* |

*Parenthesized figures indicate percent disease incidence in the various control plots. Disease incidenc in the sand blasted and inoculated control was used as the basis for the calculation of percent disease control in the plants treated with Streptomycin and with A16886.

As noted hereinabove, antibiotic A16886 and its salts exhibit anthelmintic activity in addition to antibacterial activity. Hence, antibiotic A16886 or a salt thereof can be administered to warm-blooded animals to control various internal parasites, particularly stomach and intestinal worms such as *Ascaris lumbricoides* var. *suum, Aspiculuris tetraptera, Syphacia obvelata,* and the like. As in the instance of bactericidal activity, anthelmintic activity is exhibited by each major factor; hence, anthelmintic activity is obtained when employing either factor separately, or when employing a mixture of factors.

The administration of antibiotic A16886 or a salt thereof is preferably by the oral route, for example, by inclusion of antibiotic A16886 or a salt thereof in animal feed, by administration of tablets, drenches, etc. In general, doses of from 1 to 500 milligrams per kilogram or more of animal body weight are effective in single-dose administration. Where antibiotic A16886 or a salt thereof is supplied as a constituent of a regular feed, concentrations of from 0.0001 to 0.05 percent or more give good results. A preferred range of concentration of antibiotic A16886 or a salt thereof in feeds is from 0.01 to 0.05 percent.

The anthelmintic activity of antibiotic A16886 is illustrated by the following examples.

EXAMPLE 10

In a first evaluation, antibiotic A16886 (as a mixture of the monoammonium salt of factor I and the monoammonium salt of factor II) was administered in a single dose by gavage to each of two mice infected with *Aspiculuris tetraptera* and *Syphacia obvelata* (pinworms). The dose was 500 milligrams of antibiotic A16886 per kilogram of individual animal body weight, administered in a suspension of physiological saline containing 0.125 percent of methylcellulose as suspending agent. A control group of six mice infected with *Aspiculuris tetraptera* and *Syphacia obvelata* was employed in the evaluation. Both groups were maintained under normal laboratory conditions for forty-eight hours following the dosing of the treated group. All mice were then sacrificed and examined to determine the presence and numbers of pinworms, which were as reported in the following table:

TABLE XI

| | Number of Pinworms per animal (average) | |
|---|---|---|
| | *Aspiculuris tetraptera* | *Syphacia obvelate* |
| Control | 35.0 | 41.0 |
| Antibiotic A16886 at 500 mg./kg. | 4.5 | 0.5 |

EXAMPLE 11

In another evaluation, antibiotic A16886 (as a mixture of the monoammonium salt of factor I and the monoammonium salt of factor II) was mixed with standard mouse feed to obtain a plurality of treated feeds, containing antibiotic A16886 in concentrations of 0.005, 0.01, and 0.05 percent by weight. The feeds were utilized as diets for separate groups of mice, five mice per group. Above twelve hours after initiation of the feeding, the mice were infected with *Ascaris lumbricoides* var. suum ova. Another group of five mice were fed the non-medicated feed to serve as a control but was similarly infected at the same time with *Ascaris lumbricoides* var. suum. All groups were fed their respective feed and maintained under normal laboratory conditions for a period of eight days, at which time all mice were taken off feed. On the ninth day, all mice were sacrificed and the lungs examined to determine the presence, and if present, numbers, of lesions of *Ascaris lumbricoides* var. suum.

The level of antibiotic A16886 in the diet and the average number of lung lesions per animal in each group are set forth in the following table:

TABLE XII

| Group | Average Number of Lung Lesions Per Group |
|---|---|
| Control | 2.0 |
| Antibiotic A16886 at 0.005 percent | 0.166 |
| Antibiotic A16886 at 0.01 percent | 0.33 |
| Antibiotic A16886 at 0.05 percent | 0.0 |

EXAMPLE 12

Another evaluation was conducted under the procedures reported in Example 11, except that the rates were varied. The results were as follows:

TABLE XIII

| Group | Average Number of Lung Lesions Per Group |
|---|---|
| Control | 2.2 |
| Antibiotic A16886 at 0.0005 percent | 1.2 |
| Antibiotic A16886 at 0.001 percent | 0.7 |
| Antibiotic A16886 at 0.1 percent | 0.2 |

EXAMPLE 13

In a further evaluation, the monoammonium salts of A16886I and A16886II were separately evaluated for the control of *Ascaris lumbricoides* var. suum. The evaluations were conducted in accordance with the procedure reported in Example 11 at a concentration in the diet of 0.05 percent. The results of the evaluations were as reported in the following table.

TABLE XIV

| Group | Average Number of Lung Lesions Per Group |
|---|---|
| A16886I | 0.46 |
| A16886II | 0.20 |
| Control | 2.66 |

Antibiotic A16886 can be produced by culturing a newly found and hitherto undescribed organism isolated from soil samples obtained from South America.

The organism was isolated from the above soil samples by suspending portions of the soil samples in sterile distilled water, and by streaking the suspensions on nutrient agar. The seeded nutrient agar plates were incubated at about 25°–35° C. for several days. At the end of the incubation period, colonies of the antibiotic A16886-producing organism were transferred with a sterile platinum loop to agar slants. The agar slants were then incubated to provide suitable amounts of inoculum for the production of antibiotic A16886.

The actinomycete used according to this invention for the production of antibiotic A16886 has been difficult to classify in the genus Streptomyces because of its atypical sporophore morphology. However, data on cell wall analysis indicate that the culture should be considered a species in the Streptomyces genus. Accordingly, the organism is treated as a new species and given the name *Streptomyces clavuligerus*.

This organism characteristically produces an extensive network of short, sympodially-branched aerial hyphae which eventually segment into spores. Short club-shaped side branches are formed which usually produce from one to four spores each. No substrate conidia are produced. Electron micrographs reveal smooth-walled spores. Cell wall preparations contain the L,L-isomer of diaminopimelic acid and glycine in addition to the major constituents, aspartic acid, glutamic acid, and alanine. Spores are gray en masse and primary mycelium is pale yellow to yellow-brown. No soluble pigment is produced. The culture has an optimum temperature range between 26° and 30° C. No growth occurs at 37° C. Morphologically, this culture resembles certain strains of Thermomonospora and Micromonospora.

The novel organism capable of producing antibiotic A16886 has been placed on permanent deposit without restriction as to availability with the culture collection of the Northern Utilization Research and Development Division, Agricultural Research Service, U.S. Department of Agriculture (formerly Northern Regional Research Laboratories), Peoria, Illinois, 61604, and is available to the public under culture No. NRRL 3585.

The characteristics of *Streptomyces clavuligerus* NRRL 3585 are given in the following tables. The methods recommended for the International Streptomyces Project (Shirling et al., "Methods for Characterization of Streptomyces Species," *Intern. Bull. Systematic Bacteriol.* 16: 313–340) (1966) for the characterization of Streptomyces species have been used along with certain supplementary tests. Color names were assigned according to the ISCC-NBS method described by Kelly et al. in *The ISCC-NBS Method of Designating Colors and a Dictionary of Color Names* (U.S. Department of Commerce Circ. 553, Washington, D.C. 1955). Figures in parenthesis refer to the Tresner and Backus color series (Tresner et al., "System of Color Wheels for Streptomyces Taxonomy," *Appl. Microbiol.* 11: 335–338 [1963]) and color tab designations are underlined. The Maerz and Paul color blocks (Maerz et al., *Dictionary of Color* (McGraw-Hill Book Co., Inc., New York, 1950) are enclosed in brackets. Cultures were grown at 30° C. for 14 days unless noted otherwise.

TABLE XV

| Property Observed | Characteristics of A16886 |
|---|---|
| Morphology | Sporophores are produced on an extensive aerial mycelium and consists of networks of short, sympodially-branched hyphae. Usually from one to four spores are born on short club-shaped side branches. Eventually sporophores segment to form chains of spores. Spores are 0.34–0.85μ × 0.85 × 3.3μ, averaging 0.64μ × 1.53μ. Electron micrographs reveal smooth-walled spores. Spores are not produced in the substrate mycelium. |
| Property Observed | Characteristics of A16886 |
| Cultural Characteristics on: | |
| ISP No. 2 (Yeast-Malt ext. agar) | Growth abundant, reverse grayish yellow [12K3]; aerial mycelium abundant, dark gray (G) 3ih [21B1]; no soluble pigment. |
| ISP No. 3 (Oatmeal agar) | Growth moderate, reverse pale Yellow [11Cl]; aerial mycelium fair, white (W) b [27A1]; no soluble pigment. |
| ISP No. 4 (Inorganic Salts-Starch agar) | Growth abundant, reverse grayish yellow [12B2]; aerial mycelium moderate, medium gray (GY) 2fe [45A1]; no soluble pigment. |
| ISP No. 5 (Glycerol-asparagine agar) | Growth fair, reverse pale yellow green [10B1]; aerial mycelium fair, white (W) a; no soluble pigment. |
| Tomato paste-oatmeal agar | Growth abundant, reverse grayish yellow [11E4]; aerial mycelium moderate, light grayish olive (GN) 1-½ig [21B1]; no soluble pigment. |
| Emerson's agar | Growth abundant, reverse pale yellow [11Cl]; aerial mycelium scant; no soluble pigment. |
| Bennett's agar | Growth abundant, reverse light yellow [11J2]; aerial mycelium abundant, dark grayish green (GN) 24½ih [23A3]; no soluble pigment. |
| Czapek's agar | Scant growth |
| Glucose-Asparagine agar | Growth moderate, reverse pale yellow green [10B1]; aerial mycelium fair, white (W) b [27A1]; no soluble pigment. |
| Tyrosine agar | Growth moderate, reverse pale yellow [10B2]; aerial mycelium moderate, yellowish gray (GY) 2dc [10A2]; no soluble pigment. |
| Nutrient agar | Growth fair, reverse pale yellow green [10B1]; aerial mycelium sparse, white; no soluble pigment. |
| Cultural Characteristics on: | Characteristics of A16886 |
| Calcium malate | Growth abundant, reverse pale yellow green [10B1]; aerial mycelium fair, white (W) a. |
| Action on milk | No coagulation; clearing in 17 days. |
| Nitrate reduction | Negative |
| Gelatin liquefaction | None |
| Growth response to pH changes | pH 5.0–6.0 in optimum range for growth; growth but no sporulation from pH 7.5–8.5. |
| Melanin production Peptone-iron agar and tryptone-yeast ext. broth | None |
| Temperature requirements | Growth and sporulation good from 26°–30°; no growth at 37° or above. |
| Major constituents of whole cell hydrolysates | L,L-diaminopimelic acid, glycine, glutamic acid, aspartic acid, alanine, and leucine. |

In Table XVI are set forth the results of carbon utilization tests carried out on organism NRRL 3585. In the table, the following symbols are employed:

+= growth and utilization
 −= no growth, no utilization
 (+)= probable utilization
 (−)= questionable utilization

TABLE XVI

| Carbon Utilization Pattern for NRRL 3585 | |
|---|---|
| Compound | Growth Response |
| Carbon Utilization: | |
| L-arabinose | − |
| rhamnose | − |
| fructose | − |
| D-xylose | − |
| melezitose | (−) |
| raffinose | − |
| dextrose | − |
| cellobiose | − |
| maltose | + |
| sucrose | − |
| cellulose | − |
| inositol | (+) |
| mannitol | − |
| Na glutamate | (+) |

As above noted, antibiotic A16886 can be produced by the cultivation of NRRL 3585. The culture medium employed in producing antibiotic A16886 by cultivation of the above-identified organism can be any one of several media, although as it is apparent from the above-described utilization tests, the organism is capable of using only a few carbon sources under artificial culture circumstances. Those skilled in the art will understand that the organism in a complete medium may utilize carbon sources which in such artificial circumstances are not utilized. However, for economy production, maximum yield of antibiotic, and ease of isolation of the antibiotic, certain relatively simple nutrient sources are preferable. For example, the media which are useful in the production of the antibiotic include an assimilable source of carbon such as glucose, starch, glycerine, molasses, dextrin, and the like.

Preferred sources of carbon are glucose and glycerol. Additionally, employable media include a source of assimilable nitrogen such as soybean meal, corn steep solids, yeast, cottonseed meal, beef extract, peptones (meat or soy), casein, amino acid mixtures, and the like. Preferred sources of nitrogen are peptones, soybean meal, amino acid mixtures, and the like. Among the nutrient inorganic salts which can be incorporated in the culture media are the customary salts capable of yielding sodium, potassium, ammonium, calcium, phosphate, sulfate, chloride, carbonate, and like ions.

Minor elements necessary for optimum growth and development of the organism used for the production of antibiotic A16886 can also be included in the culture medium. Such trace elements commonly occur as impurities in the other constituents of the medium in amounts sufficient to meet the growth requirements of the actinomycetes employed in this invention.

The initial pH of the culture medium can be varied. However, it has been found desirable that the initial pH of the medium be between 6.5 and 7.2. As has been observed with other actinomycetes, the pH of the medium gradually increases throughout the growth period of the organism while the antibiotic is being produced, and may attain a level of from 6.7 to 7.5 or above, the final pH being dependent at least in part on the initial pH of the medium, the buffers present in the medium, and the period of time the organism is permitted to grow.

Submerged, aerobic cultural conditions are the conditions of choice for the production of antibiotic A16886. For preparation of relatively small amounts, shake flask and surface culture in bottles can be employed; but for the preparation of large amounts, submerged aerobic culture in sterile tanks is preferred. The medium in the sterile tank can be inoculated with a sporulated suspension; but because of the growth lag experienced when a sporulated suspension is used as the inoculum, the vegetative form of the culture is preferred. By thus avoiding the growth lag, more efficient use of the fermentation equipment is realized. Accordingly, it is desirable first to produce a vegetative inoculum of the organism by inoculating a relatively small quantity of culture medium with the spore form of the organism; and when a young, active vegetative inoculum has been obtained, to transfer the vegetative inoculum aseptically to the large tank. The medium in which the vegetative inoculum is produced can be either the same as or different from the medium utilized for the large-scale production of antibiotic A16886.

The organism which produces antibiotic A16886 will grow over a wide temperature range between 25°–37° C. Optimal production of A16886 seems to occur at temperatures of 26°–30° C. In general, maximum production of the antibiotic occurs within about 36–72 hours after inoculation of the culture medium.

As is customary in aerobic, submerged culture processes, sterile air is blown through the culture medium. For efficient growth of the organism and antibiotic A16886 production, the volume of air employed in the tank production of A16886 is from 0.2 to 0.4 volume of air per minute per volume of culture. The preferred volume is 0.4 volume of air per minute per volume of culture medium.

The concentration of antibiotic activity in the culture medium can be followed readily during the fermentation period by testing samples of the culture medium for their inhibitory activity against the growth of organisms known to be inhibited by the presence of antibiotic A16886. The organisms *E. coli, Salmonella gallinarum,* and *Pseudomonas Solanacearum* have been found to be useful for this purpose. The testing of the samples can be carried out by the well-known turbidometric or cup-plate methods.

In general, maximum production of A16886 occurs within one to three days after inoculation of the culture medium in submerged aerobic culture or shake flask culture processes.

The antibiotic activity produced during the fermentation of A16886 occurs primarily in the antibiotic broth. Accordingly, isolation techniques employed in the production of A16886 are designed to permit maximum recovery of the antibiotic from the broth. Thus, for example, mycelium and undissolved solids are removed from the fermentation broth by conventional means such as filtration or centrifugation, and antibiotic A16886 can be recovered from the filtered or centrifuged broth by employing extraction or adsorption techniques.

For the recovery of A16886 by adsorption techniques, various adsorbents and ion exchange resins can be used, for example, carbon, silica gel, alumina, microcrystalline cellulose, and ion exchange resins, including insoluble crosslinked polymer resins such as the insoluble crosslinked polystyrene known as Amberlite XAD-4 (marketed by Rohm & Haas Co.). Antibiotic A16886, as obtained from fermentation, may be in either amphoteric or salt form, depending upon fermentation conditions. Regardless of which form, it can be adsorbed onto one of the above or similar adsorbents from solution in a suitable solvent. The adsorbed antibiotic A16886 or salt can then be eluted from the adsorbent by suitable elution techniques, such as by washing the adsorbent on which the antibiotic A16886 or salt thereof is adsorbed with a solvent. Where the elution is carried out by washing with a solution of, e.g., ammonium formate or sodium acetate, the process results in elution of antibiotic A16886 as the ammonium or sodium salt, respectively. Such salts are readily converted back to antibiotic A16886 in conventional procedures.

Salts of antibiotic A16886 other than ammonium or alkali metal are preferably prepared by conventional reaction of antibiotic A16886 in unmodified amphoteric form with the respective acid or base. Thus, in preparing acid addition salts, antibiotic A16886 is reacted with an inorganic or organic acid. Representative suitable acids include hydrochloric acid, hydrobromic acid, hydriodic acid, sulfuric acid, phosphoric acid, acetic acid, benzoic acid, sulfamic acid, tartaric acid, citric acid, maleic acid, succinic acid, ascorbic acid, and glycolic acid.

Antibiotic A16886 also forms salts with cations by reaction of A16886 in unmodified amphoteric form with inorganic and organic bases and salts. Exemplary of these salts are ammonium and substituted ammonium salts; alkali metal salts, such as sodium, potassium, lithium, cesium, and rubidium salts; alkaline earth metal salts such as calcium, strontium, and barium salts; and copper, zinc, magnesium, and silver salts. In the instance of organic bases, the identity of the base is not critical, although, in general, a base having a pH of, numerically, 3.0 or above in water is preferred. Representative suitable organic bases include benzylamine, methylamine, diethylamine, triethylamine, procaine, diisopropylamine, ethanolamine, cyclohexylamine, dicyclohexylamine, diphenylamine, di-n-butylamine, quinoline, and pyridylamine.

The salts of antibiotic A16886 which are pharmaceutically acceptable are generally preferred for pharmaceutical applications. However, all salts are useful as intermediates in the production, separation, and purification of antibiotic A16886. For therapeutic purposes, pharmaceutically acceptable salts are generally equivalent to antibiotic A16886; however, particular salts are occasionally preferred due to a favorable property, such as solubility, conferred by the salt-forming moiety.

In order to illustrate more fully the operation of the invention, the following additional examples are provided by way of illustration.

EXAMPLE 14
SHAKE FLASK PRODUCTION OF ANTIBIOTIC A16886

A sporulated culture of *Streptomyces clavuligerus* NRRL 3585 was produced by growing the organism on a nutrient agar slant having the following composition:

| | |
|---|---|
| Dextrin | 10.00 g. |
| Yeast Extract | 1.00 g. |
| Hydrolyzed Casein ("N-Z Amine-Type A," Sheffield Chemical Company) | 2.00 g. |
| Beef Extract | 1.00 g. |
| Meer Agar (washed three times) | 20.00 g. |
| Deionized water | 1 liter |

The pH of the medium was adjusted to pH 7.0 by the addition of sodium hydroxide.

The agar slant was inoculated with spores of *Streptomyces clavuligerus* NRRL 3585 and was incubated for 4–6 days at 30° C. The agar slant was then covered with sterile distilled water and gently scraped to remove the spores and cells as an aqueous suspension thereof. One milliliter of the resulting suspension was used to inoculate each 100 ml. portion of a vegetative medium having the following composition:

| | |
|---|---|
| Glucose | 15.00 g. |
| Soybean meal | 15.00 g. |
| Cornsteep solids | 5.00 g. |
| Calcium carbonate | 2.00 g. |
| Sodium chloride | 5.00 g. |
| Deionized water | 1 liter |

The pH of the vegetative medium was adjusted to pH 6.7 by the addition of sodium hydroxide.

The vegetative inoculum was shaken for 24–48 hours at 30° C. on a reciprocal shaker with a 2-inch stroke at 108 rpm. The inoculum so prepared was then utilized in the production of antibiotic A16886 as follows.

A production medium was prepared having the following composition:

| | |
|---|---|
| Soybean meal | 15.00 g. |
| Casein | 1.00 g. |
| Sodium nitrate | 3.00 g. |
| Glucose syrup (50 percent glucose) | 20.00 g. |
| Tap water | 1 liter |

One hundred-milliliter-portions of the production medium were placed in 500-milliliter Erlenmeyer flasks which were sterilized at 120° C. for 30 minutes. When cooled, each flask was inoculated with a five percent vegetative inoculum. The fermentation was shaken for 48–72 hours at 25°–30° C. on a rotary shaker operating at 250 rpm. During the fermentation, the medium was aerated with sterile air at a rate of 0.4 v./v./min. Isolation was carried out essentially as reported hereinbelow in Example 22.

EXAMPLE 15

Antibiotic A16886 was produced according to the process of Example 14, but utilizing a production medium having the following composition:

| | |
|---|---|
| Distillers Solubles (Nadrisol) | 5.00 g. |
| Soybean flour (Nutrisoy 200D) | 5.00 g. |
| Peanut meal | 5.00 g. |
| Blackstrap molasses | 5.00 g. |
| Oatmeal | 5.00 g. |
| Glycerol | 10.00 g. |
| Tap water | 1 liter | and utilizing instead of a rotary shaker a reciprocal shaker operating at 108 strokes per minute.

EXAMPLE 16

Antibiotic A16886 was produced according to the process of Example 14, but utilizing a production medium having the following composition:

| | |
|---|---|
| Oatmeal | 20.00 g. |
| Glycerol | 10.00 g. |
| Tap water | 1 liter |

EXAMPLE 17

Antibiotic A16886 was produced according to the process of Example 14, but utilizing a production medium having the following composition:

| | |
|---|---|
| Cottonseed flour | 20.00 g. |
| Glycerol | 10.00 g. |
| Glucose | 5.00 g. |
| Tap water | 1 liter |

EXAMPLE 18

Antibiotic A16886 was produced according to the process of Example 14, but utilizing a production medium having the following composition:

| | |
|---|---|
| Glucose | 20.00 g. |
| Soluble starch | 10.00 g. |
| Peptone (Wilson's 159) | 30.00 g. |
| Hydrolyzed casein ("N-Z amine-type A" sold by the Sheffield Chemical Company) | 4.00 g. |
| Magnesium sulfate heptahydrate | 5.00 g. |
| Molasses, blackstrap | 5.00 g. |
| Calcium carbonate | 2.00 g. |

-continued

| | |
|---|---|
| Tap water | 1100 ml. |

EXAMPLE 19

Antibiotic A16886 was produced according to the process of Example 14, but utilizing a production medium having the following composition:

| | |
|---|---|
| Glycerol | 20.00 g. |
| Soy peptone | 5.00 g. |
| Calcium nitrate | 2.00 g. |
| Sodium chloride | 0.50 g. |
| Nadrisol | 3.00 g. |
| Tap water | 1 liter |

EXAMPLE 20

Another sporulated culture of *Streptomyces clavuligerus* NRRL 3585 was produced by growing the organism on a nutrient agar slant. The slant in this instance had the following composition:

| | |
|---|---|
| Dextrin | 10.00 g. |
| Yeast extract | 1.00 g. |
| Hydrolyzed casein ("N-Z Amine-Type A") (Sheffield Chemical Company) | 2.00 g. |
| Beef extract | 1.00 g. |
| Calcium chloride heptahydrate | 0.01 g. |
| Meer agar | 20.00 g. |
| Deionized water | 1 liter |

The pH of the medium was adjusted, by addition of sodium hydroxide, to 7.0.

The agar slant was inoculated with spores of *Streptomyces clavuligerus* NRRL 3585 and incubated for 7–10 days at 30° C. The agar slants were than scraped to remove spores to which were added 2.0 ml. of sterile beef serum. Of the resulting serum spore suspension, 0.1 milliliter was then transferred to a sterile lyophile tube and freeze-dried in the form of pellets.

The pellets thus obtained were used to inoculate a vegetative medium having the following composition:

| | |
|---|---|
| Glycerol | 10.00 g. |
| Sucrose | 20.00 g. |
| Nutrisoy grits | 15.00 g. |
| Amber BYF 300 | 5.00 g. |
| Tryptone | 5.00 g. |
| Potassium biphosphate | 0.20 g. |
| Tap water | 1 liter |

The pH of the medium was 6.2 and was adjusted to 6.5 with sodium hydroxide.

EXAMPLE 21

PILOT PLANT PRODUCTION OF ANTIBIOTIC A16886

To a 40-liter stainless steel fermentor were added 24 liters of a medium having the following composition:

| | |
|---|---|
| Antifoam A (an anti-foaming agent sold by the Dow Corning Company) | 5.00 g. |
| Starch | 1125.00 g. |
| Nadrisol | 125.00 g. |
| Soybean flour grits | 500.00 g. |

-continued

| | |
|---|---|
| Glycerol | 187.50 g. |
| N-Z amine A | 125.00 g. |
| Ferrous sulfate heptahydrate | 2.50 g. |
| Cold tap water | to 24 liters |

The initial pH was 5.9 and was adjusted to pH 6.5 with approximately 20 ml. of 5 N sodium hydroxide. The medium was sterilized for 30 minutes at 120° C. and 15–18 psig., cooled, and then inoculated with a five percent vegetative inoculum produced as in Example 20. The fermentation was carried out at 30° C. for 66 hours, aerated with sterile air at the rate of 0.35 v./v./min., and agitated by a mechanical stirrer operated at 420 revolutions per minute. The terminal pH was 6.3.

Antibiotic A16886 was recovered from the broth following the isolation procedure set forth in Example 22.

EXAMPLE 22

ISOLATION OF CRUDE ANTIBIOTIC A16886 AS MONOAMMONIUM SALT

Approximately 75 liters of broth obtained as reported in Example 21 were filtered with the aid of Hyflo Super-Cel (a diatomaceous earth sold by Johns-Manville Products), 5 grams per 100 milliliters. The broth filtrate was passed over a 9.5 cm. × 130 cm. column packed with 8 liters of carbon (Pittsburgh 12 × 40), at the rate of 60 ml. per minute. The column was washed with 10 liters of deionized water (pH 5.2) and the activity adsorbed on the carbon was removed by passing 50 percent aqueous acetone over the column. The fractions containing the activity were combined, concentrated in vacuo to remove acetone, and applied to a 9.5 cm. × 140 cm. column packed with Dowex 1-X1 (a strong basic anion exchange resin sold by The Dow Chemical Co.), in the formate cycle. The column was washed with 10 liters of deionized water, and the activity was removed with 0.1 M ammonium formate. The active fractions were combined, and passed over a 9.5 cm. × 100 cm. column packed with carbon (Pittsburgh 12 × 40), at the rate of 60 ml. per minute. The column was washed with water; and the activity was then eluted with ¼ acetone:water at 60 ml. per minute, yielding 15 two-liter fractions, and thereafter with 1:1 acetone:water, yielding 18 one-liter fractions. The active fractions were combined, concentrated in vacuo to remove acetone, and lyophilized.

Forty grams of combined lyophilized preparations, each preparation as discussed above, were extracted with 4 liters of methanol by stirring magnetically for 16 hours; the methanol insolubles were filtered off and the methanol soluble portion precipitated with 5 volumes of acetone. The precipitate was separated by filtration and dried. Yield was 20.6 grams.

This preparation was dissolved in a minimum of water and applied to a 5.8 cm. × 120 cm. column packed with dextran (Sephadex G-25) at a rate of 1 ml. per minute. The activity was eluted with deionized water, and the active fractions were combined and lyophilized.

Ten grams of material obtained as described was dissolved in 256 ml. of acetonitrile:water (55:45) and applied to a 5.5 cm. × 85 cm. column packed with silica gel prepared in acetonitrile:water (7:3) solvent. Application was at the rate of 3 ml. per minute. After application of the sample, the column was eluted with acetonitrile:water (7.3) at 5 ml. per minute flow rate. The most active fractions were combined, concentrated to dryness in vacuo, and lyophilized.

Material thus obtained was a mixture of the monoammonium salts of factors I and II; it was used in the antibacterial and anthelmintic evaluations reported above, as well as in separation and purification procedures reported below.

EXAMPLE 23
SEPARATION OF FACTORS I and II OF ANTIBIOTIC A16886 MONOAMMONIUM SALT Ten grams of a preparation prepared as described in Example 22 were dissolved in 197 milliliters of acetonitrile:water (55:45) and applied to a 4.0 cm.×130 cm. column packed with 1.6 liters of microcrystalline cellulose (Avicel) in acetonitrile:water (7:3). The column was loaded at 1 ml. per minute, and eluted at 2 ml. per minute with acetonitrile:water (7:3). The elution was followed by assay and paper chromatography. As a result of the elution, a plurality of fractions was obtained, each containing predominantly one factor. The fractions of the respective factors were pooled and lyophilized.

EXAMPLE 24
PREPARATION OF ANTIBIOTIC A16886 I HYDROCHLORIDE

Antibiotic A16886I monoammonium salt, prepared and separated in accordance with the foregoing examples (200 milligrams), was dissolved in 2 ml. of water. The pH of the solution initially was 5.30; it was adjusted to pH 2.0 with 1 N HCl and then concentrated under reduced pressure, to near dryness. Water (0.5 ml.) and methanol (1.5 ml.) were added, and the desired hydrochloride salt precipitated by the addition of ten volumes of acetone. The precipitated antibiotic A16886I hydrochloride was removed by filtration, washed with acetone, and dried. Analysis showed 4.50 percent chlorine. Electrometric titration of the product in a 66 percent dimethylformamide-water solution at an initial pH of 5.0 revealed the presence of three titratable groups: $pK'a_1=3.6$; $pK'a_2=5.2$; and $pK'a_3=10.8$.

EXAMPLE 25
PREPARATION OF ANTIBIOTIC A16886I DISODIUM SALT

Antibiotic A16886I monoammonium salt (200 mgm.), prepared and separated in accordance with the preceding examples, was dissolved in 2 ml. of water. The initial pH was 5.30. The solution was then adjusted to pH 10.50 with 2.5 N NaOH and concentrated, under reduced pressure to near dryness. Methanol (1.5 ml.) was added and the salt precipitated with ten volumes acetone. The precipitated antibiotic A16886I disodium salt was removed by filtration and washed with acetone, and dried. Analysis showed 6.79 percent sodium.

EXAMPLE 26
PREPARATION OF ANTIBIOTIC A16886 IN ACID FORM

Two hundred milligrams of a mixture of the monoammonium salt of antibiotic A16886I and the monoammonium salt of antibiotic A16886II were dissolved in 40 milliliters water, and 6 milliliters of Dowex 50W-X12 (H+) resin (sold by The Dow Chemical Co.) were added. The mixture was stirred for thirty minutes and filtered, using a medium sinter glass funnel, and the filtrate (pH 2.65) was lyophilized.

Electrometric titration in a 66 percent dimethylformamide-water solution at an initial pH of 4.30 revealed the presence of three titratable groups: $pK'a_1=4.2$; $pK'a_2=5.6$; and $pK'a_3=10.4$.

We claim:
1. The compound of the formula

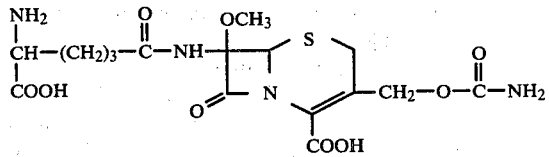

or a salt thereof.

2. A compound having the formula:

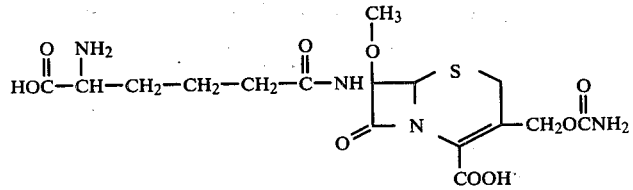

3. A compound of the formula:

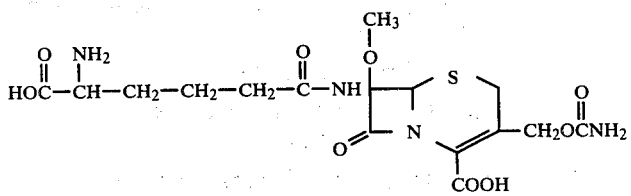

and the pharmacologically acceptable salts thereof.